United States Patent
Thoms

(10) Patent No.: US 8,363,912 B2
(45) Date of Patent: Jan. 29, 2013

(54) METHOD AND DEVICE FOR EVALUATING FLUORESCENCE IMAGE RECORDS

(76) Inventor: Michael Thoms, Bietigheim-Bissingen (DE)

( * ) Notice: Subject to any disclaimer, the term of this patent is extended or adjusted under 35 U.S.C. 154(b) by 516 days.

(21) Appl. No.: 12/531,563

(22) PCT Filed: Feb. 28, 2008

(86) PCT No.: PCT/EP2008/001567
§ 371 (c)(1),
(2), (4) Date: Jan. 27, 2010

(87) PCT Pub. No.: WO2008/113461
PCT Pub. Date: Sep. 25, 2008

(65) Prior Publication Data
US 2010/0142777 A1    Jun. 10, 2010

(30) Foreign Application Priority Data
Mar. 17, 2007  (DE) .......................... 10 2007 014 413

(51) Int. Cl.
*G06K 9/00* (2006.01)
(52) U.S. Cl. ..................................... 382/128; 356/237.3
(58) Field of Classification Search .................. 328/128; 356/237.3; 706/20; 382/128
See application file for complete search history.

(56) References Cited

U.S. PATENT DOCUMENTS

| | | | |
|---|---|---|---|
| 2005/0280809 A1* | 12/2005 | Hidai et al. | 356/237.3 |
| 2007/0118490 A1* | 5/2007 | Soderman et al. | 706/20 |
| 2008/0082000 A1 | 4/2008 | Thoms | |

FOREIGN PATENT DOCUMENTS

| | | |
|---|---|---|
| DE | 102 07 918 | 9/2003 |
| DE | 10 2004 024 494 A1 | 12/2005 |

OTHER PUBLICATIONS

International Search Report issued in corresponding International application No. PCT/EP2008/001567 mailed Aug. 4, 2008.

* cited by examiner

*Primary Examiner* — Luke Gilligan
(74) *Attorney, Agent, or Firm* — Lempia Summerfield Katz LLC

(57) ABSTRACT

The invention relates to a method and a device for evaluating fluorescence partial images representing the same object region, independently of stray light. Two partial images of the objects are produced in the red and in the green by a camera (10). A quotient image is produced in pixels from said two partial images, and the frequency of the occurrence of the image points having a pre-defined red/green ratio is determined for said quotient image. The mean values and the width are determined for the distribution curve obtained in this way. The two end variables of the distribution curve are used to calculate a threshold value. The quotient image is modified using said threshold value such that its contrast in relation to interesting details is increased.

27 Claims, 7 Drawing Sheets

Insel·100

METHOD AND DEVICE FOR EVALUATING FLUORESCENCE IMAGE RECORDS

RELATED APPLICATION DATA

This U.S. national phase application is based on international application no. PCT/EP2008/001567, filed on Feb. 28, 2008, which claimed priority to German national patent application 10 2007 014 413.1 filed on Mar. 17, 2007. Priority benefit of these earlier filed applications is hereby claimed, and the full disclosures of these earlier filed applications are hereby incorporated by reference herein.

BACKGROUND

1. Field of the Disclosure

The invention relates to a method for evaluating fluorescence image records and to a device for implementing said method.

2. Description of the Related Art

From DE 10 2004 024 494 A1, for example, it is known that diseased and healthy tissues differ by virtue of their colour. If dental enamel or similar tissue is irradiated with blue or ultraviolet light, the tissue fluoresces, whereby in the case of healthy and diseased tissues different spectral components in the fluorescent light are observed, for example different red and green components.

The change in the red component or the change in the green component can be used for the purpose of recognising diseased tissue. A particularly sensitive detection of diseased tissue is possible when the ratio of red component and green component of the fluorescent light is examined (DE 10 2004 024 494 A1).

In the known methods for recognising diseased tissues from fluorescence images it is still disadvantageous that the result is influenced by stray light (perturbing light).

SUMMARY

By means of the present invention, therefore, a method and a device for evaluating fluorescence images made from the same recording point are to be specified, with which the interfering influences of stray light or perturbing light are reduced.

In accordance with the invention this object is achieved by a method according to claim 1 and also by a device for implementing said method, according to claim 17.

In accordance with the invention, from two partial images of the same point on an object (tissue) recorded at different wavelengths a quotient image is created which reproduces, pixel by pixel, the ratio of the intensities in the first partial image and in the second partial image. For this quotient image a distribution spectrum is computed which specifies with which frequency which quotient of partial-image signals is obtained. This spectrum is characterised by a distribution curve, which has a maximum and which is characterised by a width, for example a half-width.

The shape of this distribution curve is very largely independent of perturbing-light influences. By virtue of perturbing light stemming from the environment, the distribution curve is shifted, depending on the colour of the perturbing light, only more or less far in the abscissa direction of the coordinate system that is being used for representing the distribution curve, and in some cases is also widened.

In accordance with the invention, the characteristic properties of the distribution curve that are independent of the perturbing light are now used to determine a threshold value that is used in discriminating between diseased and healthy tissue. By using this threshold value, a contrast image is created in which, for example, use is made of those pixels for which the threshold value computed as described above is exceeded.

In this way a very meaningful representation of diseased tissue regions in the contrast image is obtained, and diseased tissue regions in this contrast image that could not be seen clearly on the original overall image of the object can be made out more reliably.

Advantageous further developments of the invention are specified in dependent claims.

A contrast image that is generated in accordance with claim 2 is distinguished by particularly conspicuous discrimination of diseased and non-diseased tissue.

If the quotient image is formed directly from the intensities of the pixels of the overall image, then the quotient image, particularly in the regions of low intensity, is very noisy, since small changes in the denominator of a fraction result in large changes in the value of the fraction. In the case of a method according to claim 3, this noise caused by the formation of the quotient is attenuated, the attenuation being the greater, the larger the constant that is added to the partial-image signals. Conversely, with increasing constant the sensitivity of the diagnosis is, of course, lowered. By suitable choice of the constant—for which an initial value can be predetermined from earlier recordings, which in the individual case can then be adapted to the current conditions of the tissue recording—a compromise that is useful for practical operation can be achieved between freedom from noise and sensitivity of the diagnosis.

The method according to claim 4 takes account of greatly differing amplification factors for the pixel intensities of the partial images if such are used in the colour matching.

With the further development of the invention according to claim 5 it is ensured that as a result of the removal of noise from the formation of the quotient the dynamic range of the quotient image approximates to that of the overall image.

According to claim 6, the smoothing of the quotient image can be set in accordance with the noise component to be found in each instance in the partial images.

claim 7 specifies preferred values for the constant that can be used when generating a non-noisy quotient image.

The distribution curve derived from the quotient image can often be represented by an analytic curve, and in this case in accordance with claim 8 the interesting parameters of the distribution curve (maximum and width) can then be easily determined automatically in computational manner.

For many applications a distribution curve in the form of a Gaussian curve or normal distribution is particularly favourable, as specified in claim 9.

According to claim 10, the threshold value that is used for the discrimination between diseased and healthy tissue can be adapted to the recording conditions to be found in the given case.

In this connection, in the method according to claim 11 those parts of the distribution curve are not taken into account which are burdened with stronger system-dependent or random uncertainties.

The separation between portions of the distribution curve that are utilised and portions that are not taken into account can, in accordance with claim 12, be brought about in very simple manner and quickly.

In this connection, the values specified in claim 13 have proved to be particularly suitable to truncate foot portions of the distribution curve that are greatly affected by randomness.

With the method specified in claim 14 a still better automatic adaptation of the threshold value differentiating between diseased and healthy value to the current recording situation is obtained. In this connection, on the one hand the risk is eliminated that diseased regions are not recognised, and on the other hand the risk that healthy regions are falsely represented as diseased is kept low.

The weighting specified in claim 15 between the two partial factors that determine the threshold value has turned out to be particularly favourable.

The further development of the invention according to claim 16 permits diseased regions and the overall image of the object to be related to one another in easily graspable manner. It is easy to see which regions of the object are pathologically changed.

A device as specified in claim 18 can be constructed very easily using commercial and inexpensive components.

A device according to claim 19 is again advantageous with regard to the spatial assignment of diseased tissue regions and overall object.

In the case of a device according to claim 20, various interesting images of the object can be optionally retrieved.

BRIEF DESCRIPTION OF THE DRAWINGS

The invention will be elucidated in more detail below on the basis of an exemplary embodiment with reference to the drawing. Shown in the latter are.

DETAILED DESCRIPTION OF THE DISCLOSURE

Figure 1:
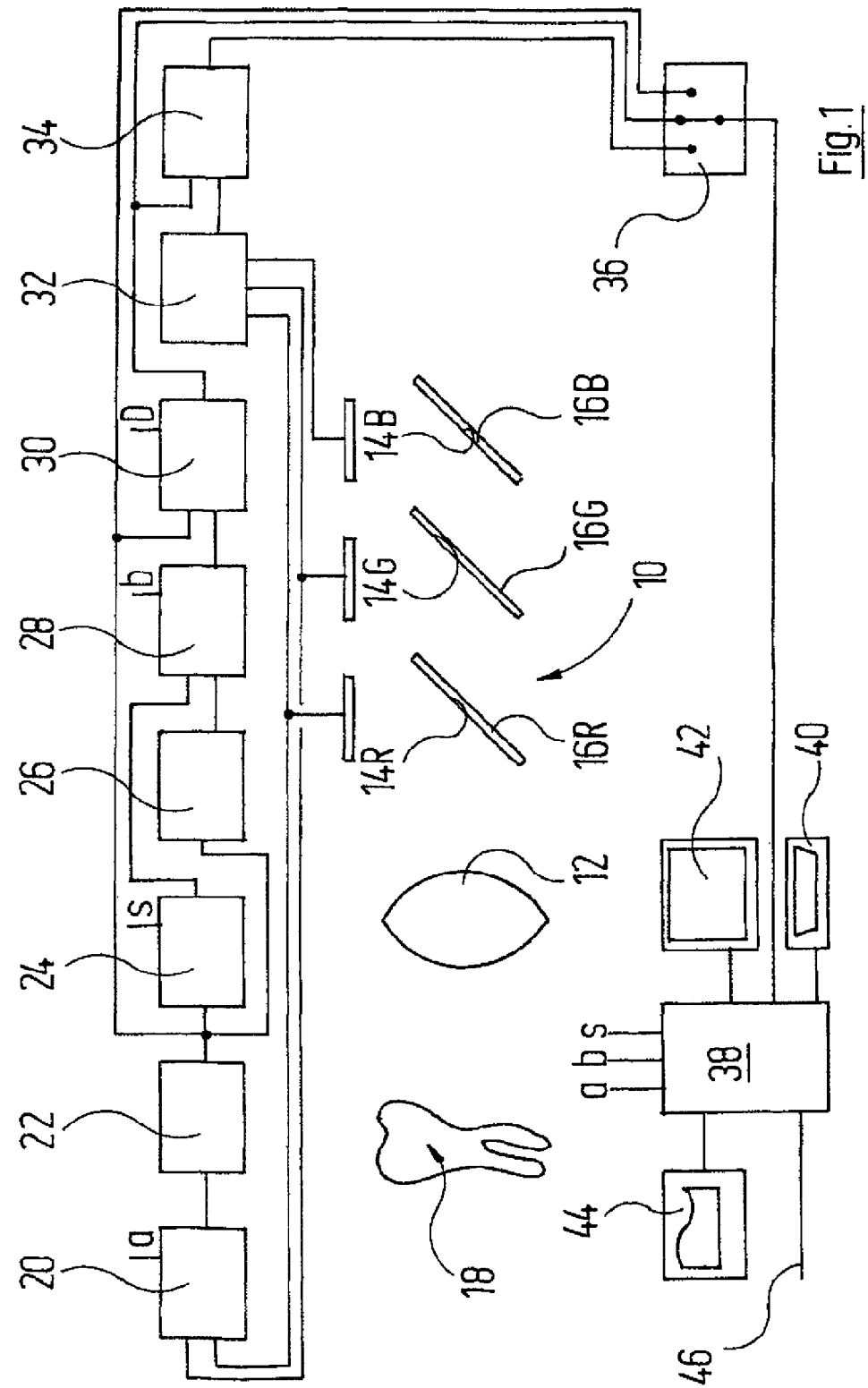
FIG. 1: a schematic representation of a dental fluorescence camera and also a block diagram of an operating and evaluating unit which is used with said camera.

In FIG. 1 a dental fluorescence-camera handpiece is denoted overall by 10. It includes an optical system 12, which is represented schematically as a single lens, three image-converters 14R, 14G and 14B for the colours red, green and blue, which via the dichroic beam-splitters 16R, 16G and 16B have the image of a tooth 18 generated by the optical system 12 applied to them.

To the extent that comments are made below that hold equally for all image-converters or all filters, the addition of the letters R, G and B is dispensed with.

For reasons of clearly arranged representation, the image-converters 14 are represented in FIG. 1 at an equal distance from the optical axis of the camera handpiece 10. In reality the spacings are different, in such a manner that the entire optical path between optical system 12 and image-converter is of equal magnitude for the various image-converters.

The image-converters 14 may be conventional CCD or CMOS image-converters and each store an image that comprises pixels arranged in lines and columns. The read-out of these pixels is effected line by line or column by column, as is known from image-converters of such a type.

For the purposes of the present description, let it be assumed that the image-converters and various switching circuits which are connected to them and which are to be described later in more detail each exhibit, where appropriate, a memory that can hold an overall image. These memories are known as such and do not need to be described in detail. Where appropriate, each of the switching circuits has an input-side memory and an output-side memory, so that the switching circuit itself and switching circuits connected thereto can in each instance access a full image.

The image-converters 14R and 14G are connected to two inputs of a computing circuit 20 which generates a quotient image from the corresponding partial images in the red and in the green. This is effected, pixel by pixel, by the signal quotient $Q_{RG}(i)$ being computed for each pixel i with intensity $I_R(i)$ or $I_G(i)$. In this connection, before the formation of the quotient a constant $a_R$ and $a_G$, respectively, which the computing circuit 20 receives from outside, is added to each of the signals $I_R(i)$ and $I_G(i)$.

The pixels Q(i) of the quotient image are consequently given by the equation $$Q(i)=(I_R(i)+a_R)/(I_G(i)+a_G)$$

whereby the condition $$a_R/a_G=\text{mean }(I_R(i)/I_G(I))$$

is preferentially complied with.

If the averaged intensities do not differ appreciably, $$a_R=a_G=a$$

can be chosen by approximation.

As a result of adding these constants $a_R$ and $a_G$, or a, it is ensured that in the case of low signal intensities $I_G(i)$ fluctuations due to noise is not reflected in large changes in the quotient.

In practice, a value for a within the range between 30 and 120, preferentially between 50 and 100, again preferentially of approximately 80, has proved worthwhile.

For very low intensities $I_R$ and $I_G$, when use is made of a single a for the intensity ratio, the value 1 is obtained by approximation, which is also obtained for healthy tissue by adjustment of the amplification factors for $I_R$ and $I_R$ in the course of colour matching. If the colour matching for $I_R$ and $I_G$ is given by very different amplification factors, it is expedient to work with different $a_R$ and $a_G$, as mentioned above.

At the output of the computing circuit 20 a quotient image is consequently obtained, the pixels of which show, in each instance, how large the ratio of red component and green component is in the original overall image of the tooth 18.

A further computing circuit 22 has the quotient image applied to it on the input side and computes from this a distribution curve of the quotient image, i.e. it establishes how large the frequency H of pixels Q(i) is for which the quotient Q(i) has a defined value q.

Figure 6:
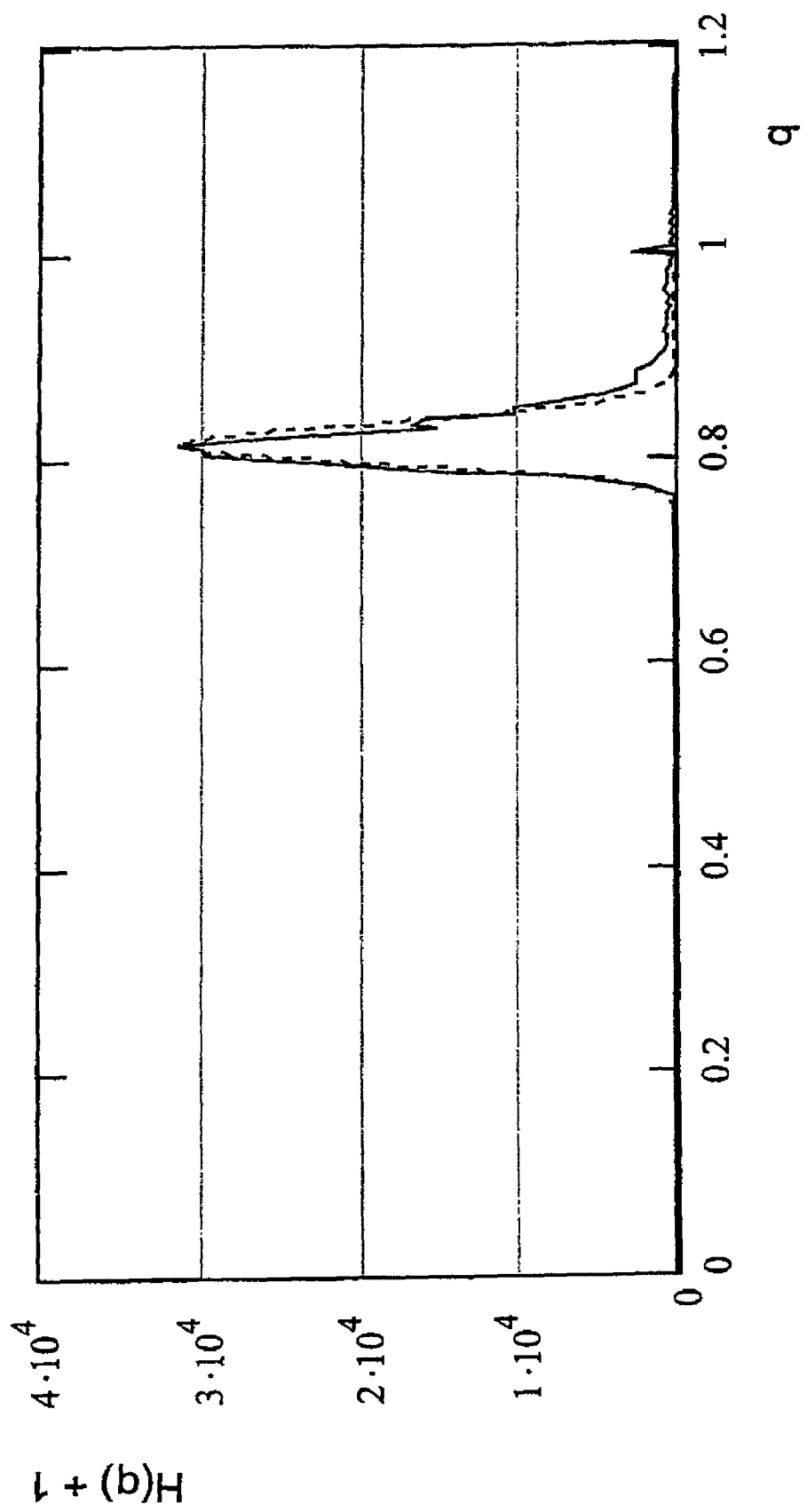
FIG. 6: the frequency distribution of pixels in the quotient image plotted over the red/green ratio of the pixel-image signals.

The result that the computing circuit 22 makes available is a distribution curve as represented in FIG. 6.

A further computing circuit 24 has this distribution curve applied to it, which determines the width for the distribution curve.

The computing circuit 24 can operate in such a way that it simply determines the half-width from the measured distribution curve. But it can also preferentially operate in such a way that an analytic curve is adapted to the measured distribution curve by least-squares fit. In this connection, a Gaussian function is preferentially chosen as distribution function.

This then has the following form in the present case $$H(q) = A \exp(-0.5(q-\mu)/\sigma^2)$$

where $\mu$ is the Q-value at which the maximum the Gaussian curve lies, and $\sigma$ is the standard deviation of the Gaussian curve.

In detail, the computing circuit 24 operates in such a way that of the measured quotient signals it only uses those having a value which is greater than a predetermined threshold s which is communicated to the computing circuit from outside. In this way it is guaranteed that randomness in the quotient of low-intensity pixels does not spread into the determination of the amplitude and of the half-width of the Gaussian function.

The output signal of computing circuit 24 is also passed to a further computing circuit 26 which computes the mean value m of the distribution curve. This may, for example, be effected analytically, taking as a basis the amplitude and standard deviation of the ascertained Gaussian function.

A further computing circuit 28 serves to compute a threshold value S which is intended to enable the discrimination between diseased and healthy tissue. This threshold value is computed by the following equation $$S = m + b^* \sigma$$

In this equation, m is the mean value, computed as described above, of the distribution curve and $\sigma$ is the standard deviation thereof.

A further computing circuit 30 has applied to it, on the one hand, the threshold value S and, on the other hand, the quotient image. It modifies the quotient image, pixel by pixel, taking into account the intensity of the individual pixel and the threshold value S.

The modification may be a change of intensity and/or a change of colour. Preferentially a change of intensity is always also undertaken.

For those pixels, the intensity of which is greater than the threshold value, the intensity is, for example, raised again; for those pixels for which the pixel intensity is lower than the threshold value, the intensity is attenuated. In this way a modified quotient image or contrast image is obtained, in which the diseased tissue regions are strongly accentuated.

These diseased tissue regions consequently appear above a weak image of the healthy regions of the tooth 18.

In a modification, the intensification of the contrast can also be undertaken in extreme manner in such a way that the pixels with intensities that are greater than the threshold value S are given a full maximum brightness, whereas the brightness 0 is assigned to the other pixels. In this way a very high-contrast image of the diseased tissue regions is obtained.

As is evident from FIG. 1, the three converters 14R, 14G, 14B are additionally connected to the inputs of a superposed circuit 32, at the output of which an overall image is consequently provided which reproduces the observed dental region in unfalsified manner.

In a downstream mixer circuit 34 the unfalsified overall image of the tooth can be concatenated with the contrast image computed in the computing circuit 30, for example by pixel-by-pixel multiplication of the intensities of the images to be concatenated.

Via a two-way switch 36 the various images mentioned above and the distribution curve of the pixels of the quotient image over the red/green ratio can optionally be passed to a computer 38 which controls the entire instrument. This computer provides the constants a, b and S which are needed in the computing circuits 20, 22 and 28. The provision of these constants is effected on the basis of fundamental values which are saved in a mass-storage device connected to the computer 38, subject to modification of corrections taking account of in accordance with the individual case, which are input on a keyboard 40 with the computer.

On a monitor 42 connected to the computer 38 the various images mentioned above can be represented. These images may also be documented permanently via a printer 44.

For the purpose of transmitting the various images to a central archive and for the purpose of exchanging patient data with a central archive, the computer 38 is connected to a data line 46 which may be part of a network.

With the diagnostic instrument described above, in particular regions of tissues coated with bacteria can be recognised, for example on tooth surfaces.

If the tooth 18 is irradiated with ultraviolet light by a source of UV light UV, then in healthy regions there is a fluorescence that is strong in the green. In surface regions of the tooth that are coated with bacteria, on the other hand, the fluorescence in the red is stronger.

With increasing attack of the bacteria on the healthy dental material, the green fluorescence image is reduced. By observation of the ratio of red and green fluorescence images an overview of healthy and diseased dental regions can consequently be acquired.

As stated above, the contrast between healthy and diseased dental tissue can be improved by the quotient of red partial image of the tooth and green partial image of the tooth being formed pixel by pixel, whereby in each instance the constant a is added to the red and green partial signals before the formation of the quotient, in order to avoid a more intense noisiness of the quotient signal.

Figure 2:
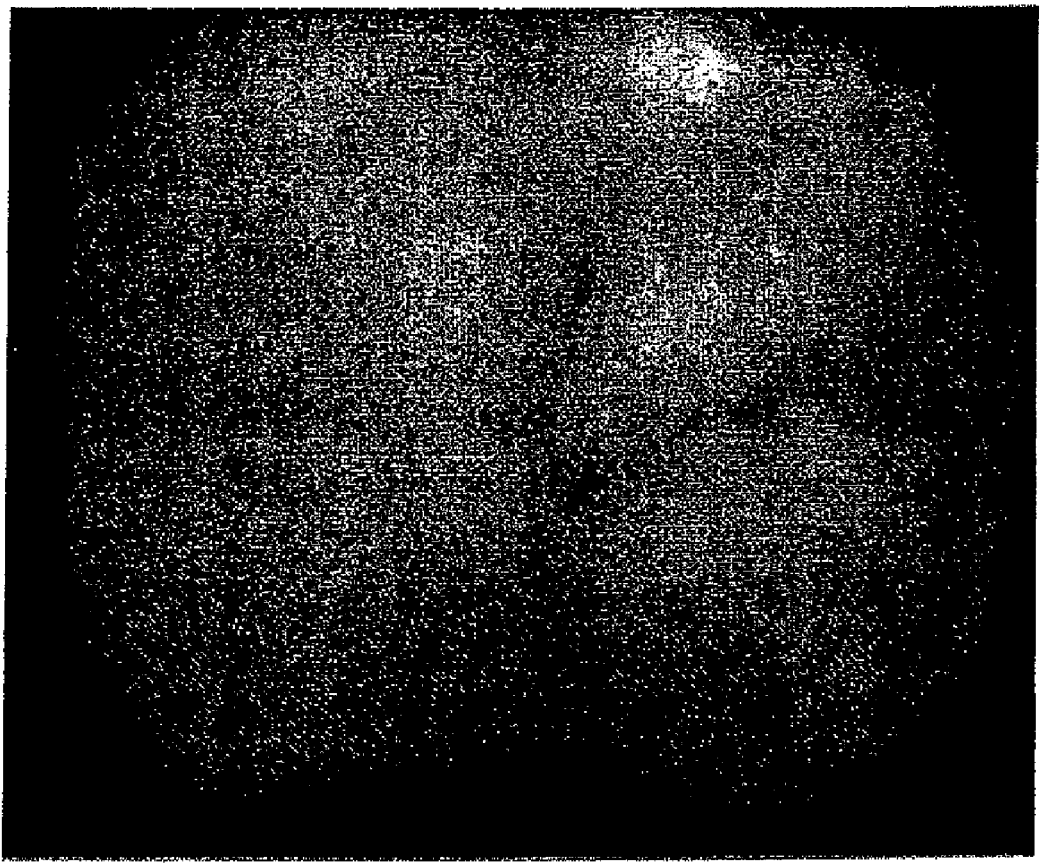
FIG. 2: an overall image of the masticatory surface of a tooth with an initial lesion or fissure.
Figure 3:
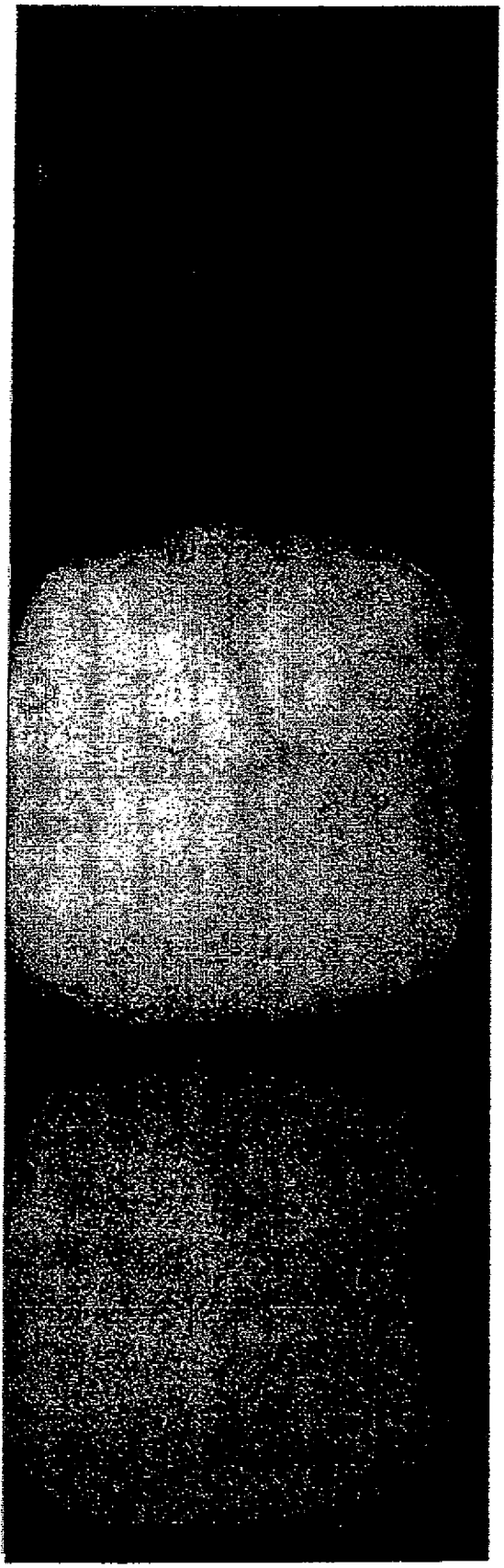
FIG. 3: three partial images of the masticatory surface shown in FIG. 2, which correspond to the colours red, green and blue.
Figure 4:
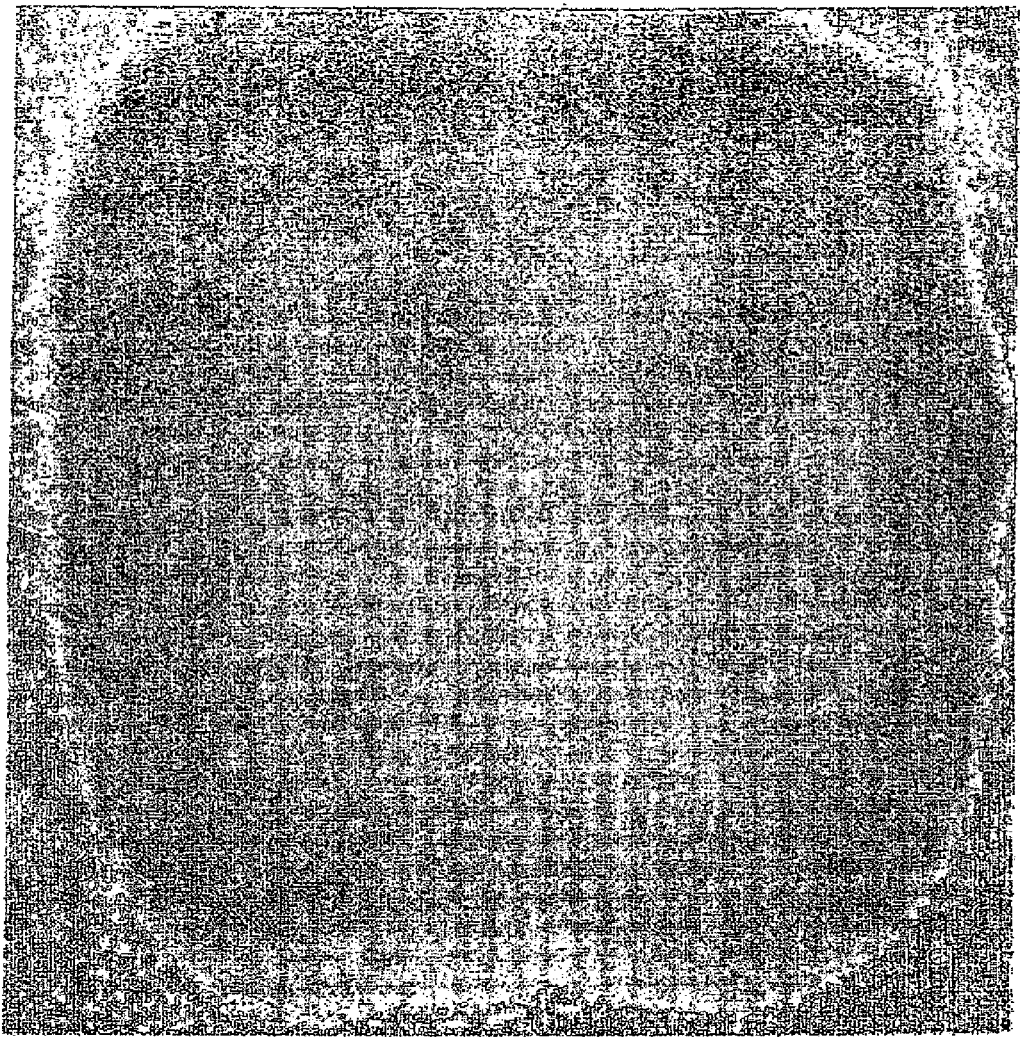
FIG. 4: a quotient image which was obtained by pixel-by-pixel division of the red image by the green image of the masticatory surface.
Figure 5:
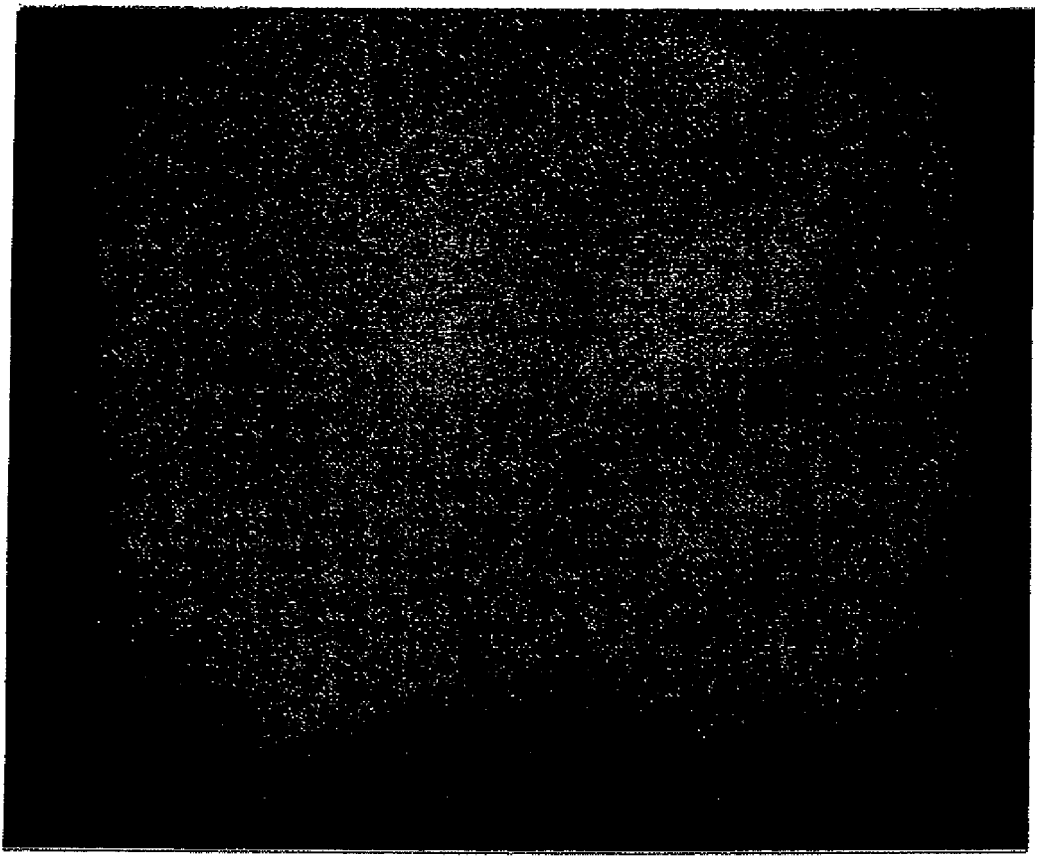
FIG. 5: a modified overall image of the masticatory surface, which was obtained by multiplication of the overall image shown in FIG. 2 by the quotient image shown in FIG. 4.

From FIGS. 2 to 4 it is evident that as a result of generating the quotient signal a better accentuation of an initial lesion which is present in the region of the fissure of the tooth is already effected.

FIG. 6 shows the frequency distribution H(q) of the pixel intensities of the quotient image.

In the course of creating this frequency distribution, values with intensity 0 in the red or green channel were not taken into account.

In the distribution curve of the brightness values of the quotient image according to FIG. 6 the maximum of the distribution curve lies at 0.813. According to what was said above, diseased regions lie at higher values of the red/green quotient q.

In FIG. 6 a Gaussian distribution obtained by a least-squares fit is represented by dashes. The adaptation of the Gaussian curve was effected only for those points of measurement at which the frequency H amounts to no less than 15% of the maximum frequency Hmax.

For this curve a standard deviation $\sigma$ of 0.0194 is computed, and a mean value of the distribution over a range around the maximum of m=0.813. As stated, for these two computations only points of the distribution curve are taken into account at which the frequency H (q) amounts to more than 15% of the maximum.

The threshold S for the computing circuit 30 is computed in accordance with the formula $$S = m + b\sigma$$

where b is chosen=3, 4.

This has the consequence that in an image with $10^6$ image points in the case of a random noise of the image signal only approximately a proportion of $1.2 \times 10^{-6}$ of the image points lie at this threshold, and still fewer above the threshold. In practice, this means that it practically does not happen that two healthy image points are falsely reported as being diseased.

Figure 7:
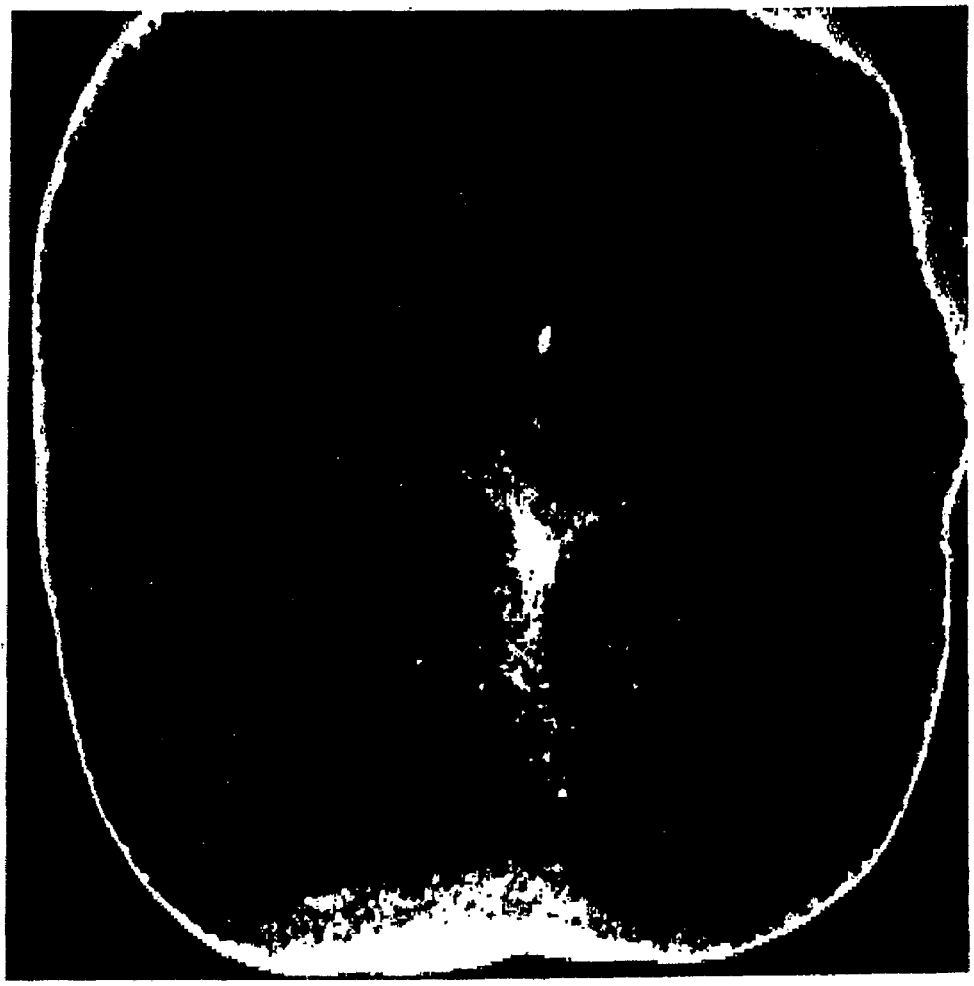
FIG. 7: a contrast image which was derived from the quotient image shown in FIG. 4, taking the pixel distribution shown in FIG. 6 into account.

In FIG. 7 the aforementioned sharp increase in contrast of the contrast image has been undertaken, with which diseased regions are given the full brightness and healthy regions are given a predetermined low brightness. It will be discerned that a point that is still inconspicuous in the overall image shown in FIG. 2 appears in the contrast image according to FIG. 7 as a diseased point. In the course of a targeted search on the basis of the contrast image, bacteria were indeed also found later at this point by staining.

The advantage of the method described above and of the device described above consists, in particular, in the fact that, irrespective of a shift of the maximum of the distribution curve according to FIG. 6 such as may be caused by extraneous light, the same result is always achieved.

Since the method described above operates with a statistical evaluation of the quotient image, in the case of intensely noisy signals healthy tissue regions are prevented from being falsely classified as diseased.

In dentistry the lesions of the dental hard tissue are provided with identifiers D0, D1, D2 and D3. With the method described above and with the instrument described above, contrast images can be created which represent, in targeted manner, lesions starting from a defined severity. This can be realised in simple manner by appropriate choice of the threshold values S.

By virtue of the procedure that has been described, perturbing light is likewise prevented from falsifying the ascertainment of the diseased regions.

The invention was described above with reference to the recognition of diseased dental hard tissue. It will be understood that the method and the device can also be used in the case of other diseased tissues, for example in the case of skin tumours or brain tumours, in which the edge of the diseased region is to be ascertained. The precondition is only that healthy regions can be characterised by a defined intensity ratio of red and green partial images, which fluctuates locally only a little.

A method and a device were described above for evaluating fluorescence images (set of images) of the same point of an object recorded at different wavelengths, which operate independently of perturbing light. With a camera, two partial images of the tissue are generated in the red and in the green. From these two partial images a quotient image is generated, pixel by pixel, and for this quotient image it is determined with which frequency image points with identical colour ratio occur, which in concrete terms accordingly have a predetermined red/green ratio. For the distribution curve obtained in this way, mean value and width are determined. These two final variables of the distribution curve are used to compute a threshold value that is used for the purpose of presetting a sharpening of contrast. By using this threshold value, the quotient image is then modified in such a way that, for example, image parts corresponding to diseased tissue regions are strongly accentuated.

The method and the device can also be used if a screening of stray light or perturbing light is not possible.

The invention claimed is:

1. Method for evaluating fluorescence partial images of differing wavelength, the method comprising:
    providing a light source;
    irradiating a common point of an object by exciting light from the light source;
    employing a device to acquire two partial images of the object;
    generating a quotient image from the two partial images by pixel-by-pixel dividing of the pixel intensities of the two partial images;
    determining for the quotient image a distribution curve which specifies with which frequency a defined quotient occurs;
    determining a threshold value depending on a width and/or a mean value of the distribution curve; and
    further generating a contrast image from the quotient image, in which the pixels of the quotient image are variably modified depending upon how their intensity lies relative to the threshold value.

2. Method according to claim 1, further including amplifying pixels of the quotient image in intensity to maximum intensity, and/or setting a first colour if their intensity is greater than the threshold value, and attenuating pixels of the quotient image in intensity to minimum intensity, and/or setting to a second colour if their intensity is lower than the threshold value.

3. Method according to claim 1, further including, in each instance, adding a constant to the pixel signals of the two partial images before generating the quotient image.

4. Method according to claim 3, wherein the ratio of the two constants is equal to the ratio of the mean values of the pixel intensities of the two partial images.

5. Method according to claim 4, wherein the same constant is added to the pixel signals of both of the two partial images.

6. Method according to claim 3, wherein the constant added to the pixel signals of the two partial images is chosen in a manner depending on the signal-to-noise ratio of the two partial images.

7. Method according to claim 6, further including exciting blue light or UV light from the light source, and generating a first partial image of the two partial images in the red and a second partial image of the two partial images in the green and wherein the constant to be added amounts to between 30 and 120.

8. Method according to claim 7, wherein the constant to be added is between 50 and 100.

9. Method according to claim 7, wherein the constant to be added is about 80.

10. Method according to claim 1, determining the width of the distribution curve of the quotient image in such a manner that an analytic distribution function is adapted to the distribution curve, by a least-squares fit, and wherein one or more of the width of the distribution curve, the maximum of the distribution curve, and/or the mean value of the distribution curve is/are predetermined by the corresponding values of the analytic curve.

11. Method according to claim 10, wherein the analytic distribution function is a Gaussian function.

12. Method according to claim 1, further including computing the threshold value in a manner depending on the mean value of the distribution curve.

13. Method according to claim 12, wherein regions of the distribution curve for which the frequency falls below a predetermined minimum value are left out of consideration.

14. Method according to claim 13, further including computing the mean value of the distribution curve taking into account those regions of the curve in which the amplitude is greater than a predetermined fraction of the maximum of the distribution curve.

15. Method according to claim 14, wherein the predetermined fraction amounts to between 0.05 and 0.3.

16. Method according to claim 15, wherein the predetermined fraction amounts to between 0.1 and 0.2.

17. Method according to claim 15, wherein the predetermined fraction is about 0.15.

18. Method according to claim 12, further including determining the threshold value from the mean value of the distribution curve and from the width of the distribution curve multiplied by a constant.

19. Method according to claim 18, wherein the constant amounts to between 2 and 5.

20. Method according to claim 19, wherein the constant is about 3.5.

21. Method according to claim 1, further including concatenating a non-filtered overall image or a partial image of the object with the contrast image.

22. Method according to claim 21, wherein the non-filtered overall image or the partial image is multiplied by the contrast image.

23. A device for evaluating fluorescence partial images of differing wavelength, the device having (a) a camera which provides at least two partial images of differing colour of an object, (b) a computing circuit which generates a quotient image from the two partial images by dividing, pixel by pixel, the pixel signals of a first partial image of the at least two partial images by those of a second partial image of the at least two partial images, (c) an analyser which generates a distribution curve of the quotient image which represents the frequency of the occurrence of pixels with a predetermined colour ratio in the quotient image and which determines the maximum and/or the width of this distribution curve, and (d) a contrast-image computing circuit which, using at least those pixels of the quotient image which exceed a predetermined threshold value, forms the pixels of a contrast image.

24. A device according to claim 23, wherein the camera includes a CCD or CMOS image-converter for generating RGB partial images for the three colours red, green and blue.

25. A device according to claim 23, further having a concatenating circuit which concatenates an overall image or a partial image generated by the camera with the contrast image.

26. A device according to claim 25, wherein the concatenating circuit multiplies the overall image or the partial image by the contrast image.

27. A device according to claim 23, further having an indicating instrument by which optionally the overall image, the contrast image or a concatenated overall image can be represented.

* * * * *